US005113862A

United States Patent [19]
Mortazavi

[11] Patent Number: 5,113,862
[45] Date of Patent: May 19, 1992

[54] BLOOD OXYGEN SENSOR HAVING LEAKAGE COMPENSATION

[75] Inventor: Said Mortazavi, Granada Hills, Calif.

[73] Assignee: Siemens Pacesetter, Inc., Sylmar, Calif.

[21] Appl. No.: 587,883

[22] Filed: Sep. 25, 1990

[51] Int. Cl.$^5$ .............................................. A61B 5/00
[52] U.S. Cl. .............................. 128/633; 128/419 PG; 128/666; 356/41
[58] Field of Search ............... 128/633, 634, 664–666, 128/419 PG; 356/41

[56] References Cited

U.S. PATENT DOCUMENTS

| | | | |
|---|---|---|---|
| 3,474,353 | 10/1969 | Keller | 331/113 |
| 3,825,016 | 7/1974 | Lale et al. | 128/419 P |
| 3,901,247 | 8/1975 | Walmsley | 128/419 PG |
| 4,120,307 | 10/1978 | Jirak et al. | 128/419 PT |
| 4,230,120 | 10/1980 | McDonald | 128/419 PT |
| 4,237,897 | 12/1980 | Beane et al. | 128/419 P |
| 4,390,020 | 6/1983 | Herpers | 128/419 PG |
| 4,399,820 | 8/1983 | Wirtzfeld et al. | 128/633 |
| 4,535,774 | 8/1985 | Olson | 128/419 PG |
| 4,590,941 | 5/1986 | Saulson et al. | 128/419 PG |
| 4,727,879 | 3/1988 | Leiss et al. | 128/633 |
| 4,750,495 | 6/1988 | Moore et al. | 128/633 |
| 4,791,935 | 12/1988 | Baudino et al. | 128/633 |
| 4,813,421 | 3/1989 | Baudino et al. | 128/633 |
| 4,815,469 | 3/1989 | Colen et al. | 128/633 |
| 5,040,538 | 8/1991 | Mortazavi | 129/633 |

*Primary Examiner*—Ruth S. Smith
*Assistant Examiner*—Robert L. Nasser, Jr.
*Attorney, Agent, or Firm*—Leslie S. Miller

[57] ABSTRACT

An improved blood oxygen sensor apparatus having a special leakage compensation circuit that allows proper initialization of the oxygen sensor regardless of the value of leakage resistance which typically might be present in parallel with the oxygen sensor. During an initialization mode, in which a capacitor arranged in parallel with oxygen sensor is charged by a small initialization current, the leakage compensation circuit monitors the capacitor voltage and controllably increases the current if it is determined that the capacitor is charging at an insufficient rate, due to unspecified leakage resistance. This enables the oxygen sensor to be properly initialized such that it can thereafter accurately measure blood oxygen levels.

35 Claims, 6 Drawing Sheets

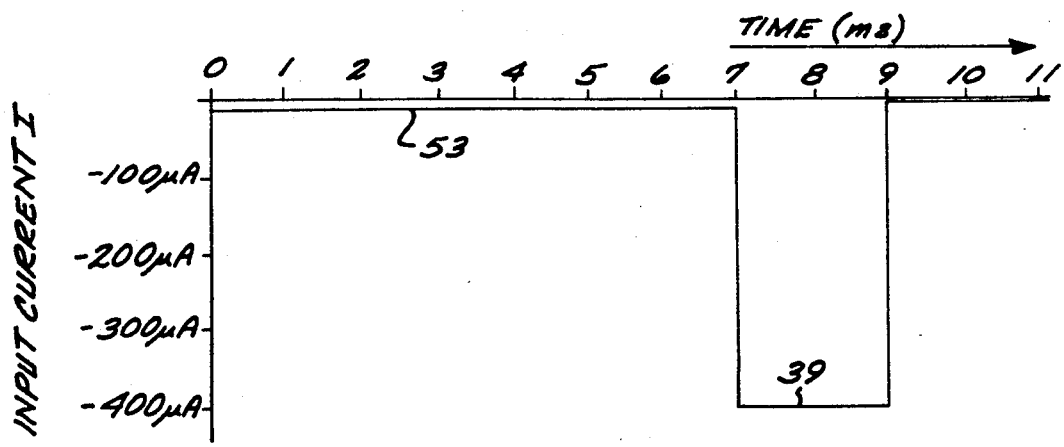
FIG.3A
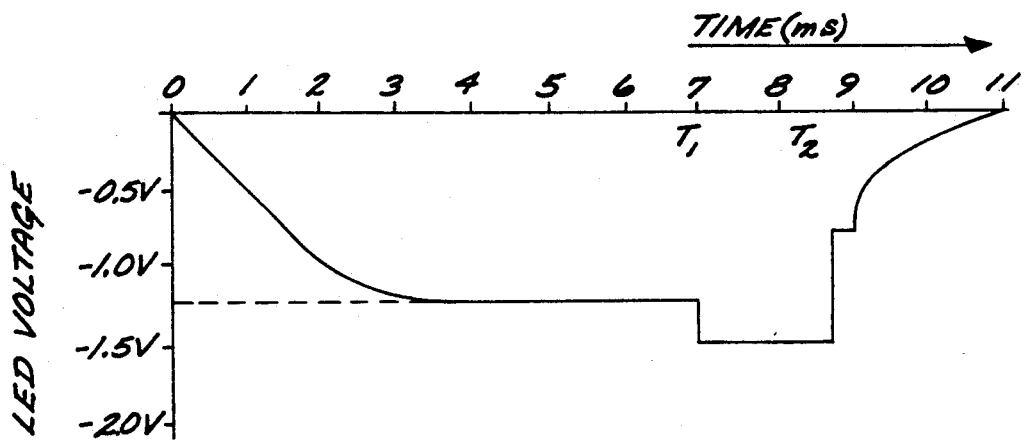
FIG.3B
FIG.3C
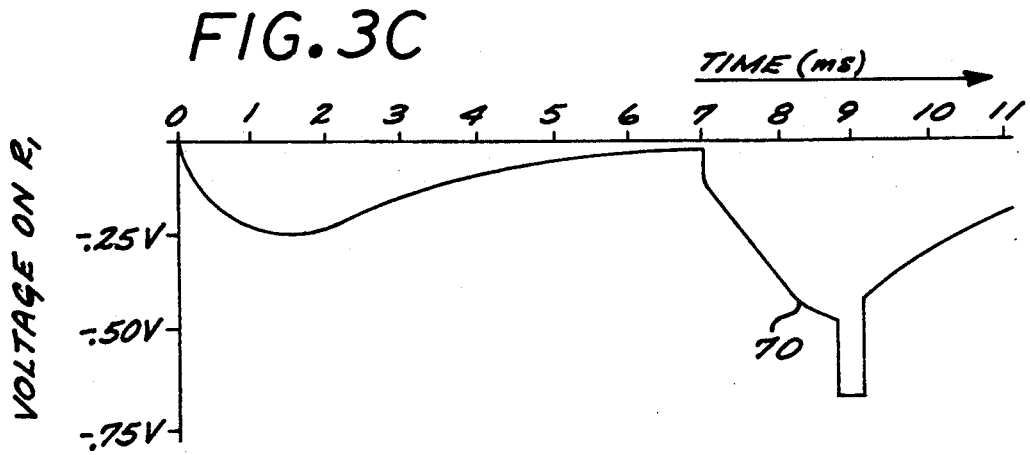

BLOOD OXYGEN SENSOR HAVING LEAKAGE COMPENSATION

BACKGROUND OF THE INVENTION

This invention relates generally to blood oxygen sensors of the kind that are useful in cardiac pacemakers, determining oxygen content by measuring the blood's reflectivity, and, more particularly, to leakage compensation circuits and methods for use in such blood oxygen sensors.

The cardiac pacemaker is perhaps one of the best known electronic marvels of modern medicine, and the implantation of a pacemaker in a patient has become almost a routine operation. The pacemaker pulses the patient's heart continuously over an extended period of time, or in the case of demand pacemakers, monitors the heart's natural operation and provides stimulating pulses only when the heart skips a beat. Pacemakers allow patients with heart problems that otherwise would have been fatal or incapacitating to resume relatively normal lives.

It will be realized by those skilled in the art that the modern pacemaker is a highly complex device, capable of event sensing, two-way telemetry, and sensing and pacing in either or both of the atrium and the ventricle of the heart. Such pacemakers may be finely tuned by the physician subsequent to implant, and the parameters adjusted to provide optimum pacing performance.

Despite the sophistication of such pacemakers, they are a compromise due to a single major difference between the healthy heart and a paced heart—namely, the response to activity or exercise. Variations in the cardiac stroke volume and systemic vascular resistance occur in the cardiovascular system due to physiological stresses such as exercise, temperature changes, postural changes, emotion, hypoglycemia, Valsalva maneuvers, etc.

To maintain adequate perfusion pressure and cardiac output under these stresses, it is necessary to adjust heart rate. The healthy heart might beat at 60 or fewer beats per minute during repose or sleep, and at 120 or more beats per minute during strenuous exercise, for example. The heart paced by a pacemaker that is non-rate responsive will typically beat at a constant rate of approximately 70 beats per minute.

It will be appreciated that the constantly-paced heart will supply more blood than is needed during sleep, and might even prevent the patient from sleeping restfully. Even more seriously, patients paced at 70 beats per minute experience substantial difficulty in engaging in strenuous activity. Even a moderate level of activity such as walking will cause difficulty in some patients. It is apparent that a pacemaker whose rate varies in response to physiological need represents a highly desirable device that will enable patients requiring pacemakers to lead normal, active lives.

Physiologically-responsive cardiac pacing must optimize cardiac rate to the level of metabolic need in the absence of normal variable cardiac rate. The simplest solution to this problem is atrial tracking pacing, where the patient has a full or partial AV block and a dual chamber pacemaker pulses the ventricle in response to normal cardiac activity sensed in the atrium. However, this technique is not possible in many patients with sinus bradycardia or atrial fibrillation, and so rate-responsive pacing is necessary to mimic the normal variable cardiac rate.

A variety of physiologically-responsive pacing systems have been proposed, which utilize a variety of physiological parameters as the basis for varying cardiac rate. These parameters include blood temperature, various sensed timing signals from the heart, pressure measured within the heart, respiratory rate, nervous system activity, physical activity, and blood chemistry.

Systems responsive to various blood chemistry parameters such as blood oxygen saturation are particularly worthwhile and effective. U.S. patent application Ser. No. 07/403,208, filed Sep. 5, 1989 and entitled "Oxygen Content Pacemaker Sensor and Method," which is assigned to the same assignee as this invention, discloses one such blood oxygen saturation sensor. That application is hereby incorporated herein by reference. The disclosed sensor includes an optical detector for measuring the mixed venus oxygen saturation, typically in the right heart. A diminution in the mixed venus oxygen saturation is used to produce a higher paced cardiac rate. The speed of this system is comparable to the time constant of the body, thereby enhancing its effectiveness.

The blood oxygen sensor disclosed in the prior application includes a light-emitting diode, i.e., LED, positioned within the right heart and arranged such that any light it emits is directed at the blood within the right heart, which reflects the light to an adjacent phototransistor. The amount of light so reflected is related to the blood's oxygen content. The phototransistor is part of a circuit that is connected in parallel with the LED. When an electrical current pulse is supplied to the LED, the phototransistor circuit begins integrating the resulting phototransistor current. When the integrated voltage reaches a predetermined threshold, the phototransistor circuit latches and diverts the current pulse from the LED, to terminate its generation of light. The time delay from initiation of the current pulse to latching of the phototransistor circuit is inversely related to the blood's oxygen level.

The blood oxygen sensor described briefly above operates very effectively in providing an accurate, repeatable measure of blood oxygen content. Sometimes, however, inaccuracies can result from the presence of unspecified resistance values arranged in parallel with the LED and phototransistor circuit. This resistance, which can arise from the intrusion of fluid into the electrical lead and/or lead connector associated with the sensor, robs electrical current otherwise intended to drive the LED and thus prevents a proper initialization of the sensor prior to supplying the current pulse to the LED.

In this case, the initialization of the sensor may not be fully accomplished by the time the current pulse is supplied to the LED. This could cause the circuit to prematurely latch, giving no indication of blood oxygen content. In this case, a rate-responsive pacemaker depending on the sensor would be unable to increase in rate. Thus, it is apparent that a compensation scheme is highly desirable.

It should therefore be appreciated that there is a need for an improved blood oxygen sensor that operates effectively to measure blood oxygen content, even in conditions where an unspecified resistance is arranged in parallel with the sensor. The present invention fulfills this need.

SUMMARY OF THE INVENTION

The present invention is embodied in a blood oxygen sensor apparatus of the kind that includes a light-emitting diode (i.e., LED) for selectively illuminating the blood and a photosensor for sensing the intensity of light reflected by the blood, with a leakage compensation circuit correcting for the presence of an unspecified resistance arranged in parallel with the LED. Detection means are responsive to the intensity signal produced by the photosensor, for determining the blood's oxygen content. To properly initialize the sensor apparatus prior to application of a current pulse to the LED, initialization means are included for supplying a prescribed initialization current to the LED during an initialization mode. This charges a capacitor arranged in parallel with the LED to a predetermined voltage that is slightly less than an onset voltage at which the LED emits substantial light. After this initialization mode, the pulse means supplies the current pulse to the LED, which is substantially greater than the initialization current, such that the LED emits substantial light for reflection by the blood and sensing by the photosensor and detection means. In accordance with the invention, the initialization means controllably increases the initialization current with time, to compensate for the presence of any resistance arranged in parallel with the capacitor and LED. This enables the sensor apparatus to charge the capacitor to its prescribed voltage efficiently and without risk of prematurely causing the detection means to mistake the initialization current for the detection of light by the photosensor.

More particularly, the blood oxygen sensor apparatus of the invention has particular utility when the detection means includes integrator means for integrating the intensity signal produced by the photosensor, and comparator means for comparing the integrated voltage signal with a predetermined threshold. The time delay from initiation of the measurement mode, i.e., the start of the current pulse, until the integrated voltage signal reaches the threshold, is inversely related to the blood's oxygen level. The comparator means can be configured such that when the integrated voltage signal reaches the threshold, the comparator means latches and thereafter accepts a substantial portion of the light-generating current previously supplied to the LED. This reduces the voltage applied to the LED below the onset voltage.

The photosensor can include a phototransistor, and the integrator means and comparator means together can include a second transistor and first and second resistors. The phototransistor is arranged with its emitter connected to the LED's cathode and its collector connected through the first resistor to the LED's anode. The second transistor is arranged with its emitter connected to the LED's anode and its collector connected through the second resistor to the LED's cathode. In addition, the phototransistor's base is connected to the second transistor's collector, and the second transistor's base is connected to the phototransistor's collector. By this arrangement, phototransistor current generated in response to the LED's emission of light charges the stray capacitance present at the phototransistor's collector. Eventually, this voltage reaches a point where the second transistor is biased on, which, in turn, biases on the phototransistor and latches the circuit. Thereafter, the electrical current previously supplied to the LED is diverted through this phototransistor circuit and the LED ceases further light generation. As noted in the above-identified application, the integration node could be other points, such as the base of the phototransistor.

In a more detailed feature of the invention, the initialization means operates to charge the capacitor arranged in parallel with the LED substantially linearly, at a rate that is insufficient to prematurely latch the phototransistor circuit. The initialization means accomplishes this charging by generating a voltage ramp reference signal and by comparing the capacitor voltage with that ramp reference signal and adjusting the initialization current in accordance with the outcome of the comparison. Thus, for example, if the capacitor voltage is sensed to be rising at a rate less than the rate of the ramp reference signal, it is deduced that the unknown parallel resistance has a lower than anticipated value and the initialization current is increased correspondingly, to compensate for it. In another more detailed feature of the invention, the comparator means compares the capacitor voltage with the ramp reference signal only at discrete times, adjusting the initialization current only in discrete steps.

In an alternative embodiment, the comparator means, instead of comparing the capacitor voltage signal with a voltage ramp reference signal, periodically varies a capacitance in the circuit and compares a voltage dependent on the sensor signal (and the varying capacitance) with a reference voltage. The magnitude of the compared voltage should be at least as large as the reference voltage. If it is not, then the initialization current is adjusted. Again, the comparator means can perform the comparisons only at discrete times, increasing the initialization current in discrete steps in accordance with the outcomes of the successive comparisons.

It will be appreciated by those skilled in the art that the compensation system of the present invention will act to prevent premature latching of the sensor circuit due to incomplete initialization. In addition, by ensuring that the initialization process is highly consistent and accurately performed, the present invention makes the measurement of blood oxygen much more accurate.

Other features and advantages of the present invention should become apparent from the following description of the preferred embodiments, taken in conjunction with the accompanying drawings, which illustrate, by way of example, the principles of the invention.

BRIEF DESCRIPTION OF THE DRAWINGS

FIG. 3(a) is a timing diagram showing the electrical current supplied by a prior art sensor drive circuit to an oxygen sensor like that of FIG. 2.

FIG. 3(b) is a timing diagram showing the voltage across the oxygen sensor of FIG. 2 that arises from the electrical current of FIG. 3(a).

FIG. 3(c) is a timing diagram showing the voltage across the resistor $R_1$ in the oxygen sensor of FIG. 2 that arises from the electrical current of FIG. 3(a).

DESCRIPTION OF THE PREFERRED EMBODIMENTS

Figure 1:
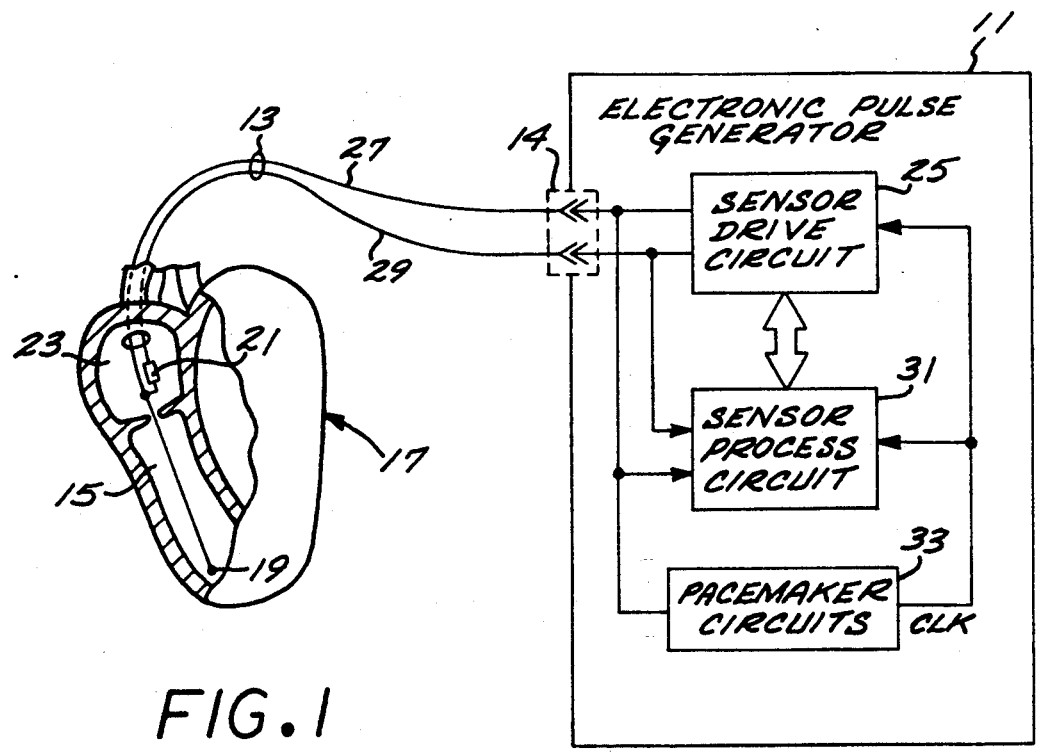
FIG. 1 is a schematic/block diagram of a blood oxygen saturation sensor apparatus embodying the present invention, shown with its oxygen sensor implanted in a heart.

With reference now to the drawings, and particularly to FIG. there is shown a pacemaker system having an oxygen sensor apparatus embodying the present invention, shown implanted into a patient. The pacemaker system includes two components, the first being an electronic pulse generator 11, and the second being a pacing lead 13. One end of the pacing lead is connected through a connector 14 to the pulse generator, while the other end is implanted through a vein into the right ventricle 15 of the patient's heart 17. Disposed on the pacing lead, proximal to the lead's distal end 19, is an oxygen sensor 21. In FIG. 1, the sensor is depicted in the heart's right atrium 23, although it will be appreciated that the sensor alternatively could be located in a vein leading to the heart or in the heart's right ventricle. The illustrated pacing lead is unipolar, although bipolar leads are well known in the art and could alternatively be used. In addition, the illustrated pulse generator is a single chamber device, although the principles of the invention are equally applicable to dual chamber devices.

The electronic pulse generator includes a sensor drive circuit 25 having a current source for supplying a prescribed electrical current over first and second conductors 27 and 29, respectively, of the pacing lead 13 to the oxygen sensor 21. The resulting voltage is monitored and evaluated by a sensor process circuit 31 of the pulse generator, to detect the blood's oxygen level. Appropriate timing signals are exchanged by the sensor drive circuit and the sensor process circuit. Additional pacemaker circuits 33 are provided for other, unrelated aspects of the pacemaker system.

Figure 2:
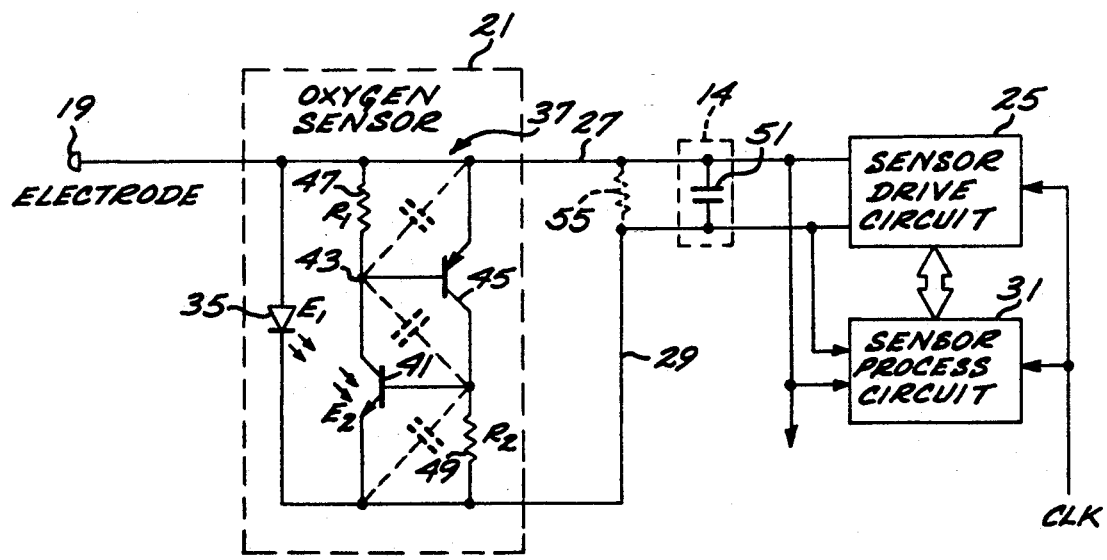
FIG. 2 is a schematic/block diagram of one suitable electrical circuit configuration for the oxygen sensor, shown in combination with the sensor drive and sensor process circuits of FIG. 1.

With reference now to FIG. 2, the oxygen sensor 21 includes a light-emitting diode, i.e., LED, 35 and a phototransistor circuit 37 that are both connected between the two conductors 27 and 29 of the pacing lead 13. To detect the blood's oxygen level, a current pulse 39 (FIG. 3(a)) is applied over the pacing lead to the oxygen sensor such that the LED emits light $E_1$ that is directed at the blood. The phototransistor circuit includes a phototransistor 41 that detects light $E_2$ reflected from the blood, to generate a photocurrent that is integrated by the circuit. During this integration time, substantially all of the current is conducted through the LED, which generates a voltage level of about $-1.6$ volts, as shown in FIG. 3(b). The light $E_1$ preferably has a wavelength of about 660 nanometers, which is a wavelength at which the blood's reflectivity varies substantially with oxygen level.

The photocurrent is integrated at an integrating node 43, which is the collector terminal of the phototransistor 41. The voltage at this node is depicted in FIG. 3(c). When the node voltage reaches a predetermined threshold, the phototransistor circuit 37 latches on, to divert current from the LED 35. This sharply lowers the voltage between the two conductors 27 and 29 of the pacing lead 13, as shown in FIG. 3(b). The sensor process circuit 31 detects this voltage reduction and deduces that the phototransistor circuit has latched. The time delay from initiation of the current pulse at time $T_1$ to latching of the phototransistor circuit at time $T_2$ is inversely related to the photocurrent and thus inversely related to the blood's oxygen level. The electronic pulse generator 11 then appropriately utilizes this information to determine an appropriate pulse rate for the patient's heart 17.

The phototransistor circuit 37 includes the phototransistor 41, a second transistor 45, a first resistor $R_1$ 47, and a second resistor $R_2$ 49. The phototransistor preferably is an npn transistor, and the second transistor is preferably a pnp transistor. The collector terminal of the second transistor is connected to the base terminal of the phototransistor, and the collector terminal of the phototransistor is connected to the base terminal of the second transistor. In addition, the second transistor's emitter terminal is connected to the LED's anode, and the phototransistor's emitter terminal is connected to the LED's cathode. In addition, the resistor $R_1$, which preferably has a resistance substantially larger than that of the resistor $R_2$ (e.g., 20 megohms and 220 kilohms, respectively), is connected between the base and the emitter terminals of the second transistor, and the resistor $R_2$ is connected between the base and emitter terminals of the phototransistor.

The voltage at the integrating node 43 of the phototransistor circuit 37 integrates the photocurrent generated by the phototransistor 41 because of capacitance associated with the base-emitter and base-collector junctions of the phototransistor and the second transistor 45. This capacitance is shown in phantom lines in FIG. 2. Eventually, the voltage at the integrating node forward biases the second transistor such that it begins to supply current from its collector terminal. This, in turn, forward biases the phototransistor, and the phototransistor circuit thereby immediately latches on. Most of the current supplied by the sensor drive circuit 25 to the oxygen sensor 21 then flows through the oxygen sensor, bypassing the LED 35 and terminating the LED's emission of light $E_1$.

To properly initialize the phototransistor circuit 37 and ensure that it does not latch on prematurely, i.e., when the current pulse 39 (FIG. 3(a)) commences, at time $T_1$, a small initialization current is initially supplied to the circuit prior to the current pulse. This initialization current is intended to charge a feedthrough capacitor 51 associated with the connector 14 to a predetermined voltage slightly less than the LED's onset voltage, which onset voltage is typically about 1.35 volts, at which the LED 35 begins emitting substantial light. This initialization current is depicted in FIG. 3(a) by the reference numeral 53. Initialized in this fashion, the LED immediately begins emitting light $E_1$ when the current pulse commences at time $T_1$.

An important constraint on the initialization current is that it not exhibit any rapid increases in voltage magnitude. Otherwise, the initialization current could be conducted through the leakage capacitance of the phototransistor 41 and second transistor 45, to charge the integrating node 43 to a sufficient voltage to forward bias the second transistor and thereby latch the phototransistor circuit 37. It thus will be noted in FIG. 3(c) that the voltage at the integrating node does in fact increase during the initialization period; however, because the initialization voltage does not undergo a rapid increase in magnitude, this voltage is never sufficient to bias on the second transistor.

It is sometimes the case that leakage resistance, of unspecified value, can be arranged in parallel with the LED 35 and the phototransistor circuit 37. This resistance is identified by the reference numeral 55. This resistance, which can arise from the intrusion of fluid into the pacing lead 13 and/or the lead connector 14, robs electrical current otherwise intended to initially charge the feedthrough capacitor 51, and then to go through the LED 35. This prevents a proper initialization of the oxygen sensor 21, because the feedthrough capacitor 51 never reaches its predetermined voltage slightly less than the LED's onset voltage. Since the value of the resistance is not generally known, but rather can vary over a wide range (e.g., 50 kilohms to 4 megohms), its presence cannot be compensated for merely by increasing the initialization current 53 by a specific amount.

In accordance with the invention, a proper initialization of the oxygen sensor 21 is ensured by specially configuring the sensor drive circuit 25 to controllably increase the initialization current so that the voltage on the feedthrough capacitor 51 charges uniformly to its prescribed voltage, regardless of the value of any parallel leakage resistance 55. To achieve this result, the sensor process circuit 31 periodically monitors the voltage across the two conductors 27 and 29 of the pacing lead 13 and compares that voltage with an internal reference. When it is determined that the voltage is increasing at an insufficient rate, it is deduced that the leakage resistance is robbing some of the initialization current and the sensor drive circuit thereupon is conditioned to increase the initialization current accordingly. Two alternative embodiments of the sensor drive circuit and sensor process circuit for achieving this result are disclosed below.

Figure 4:
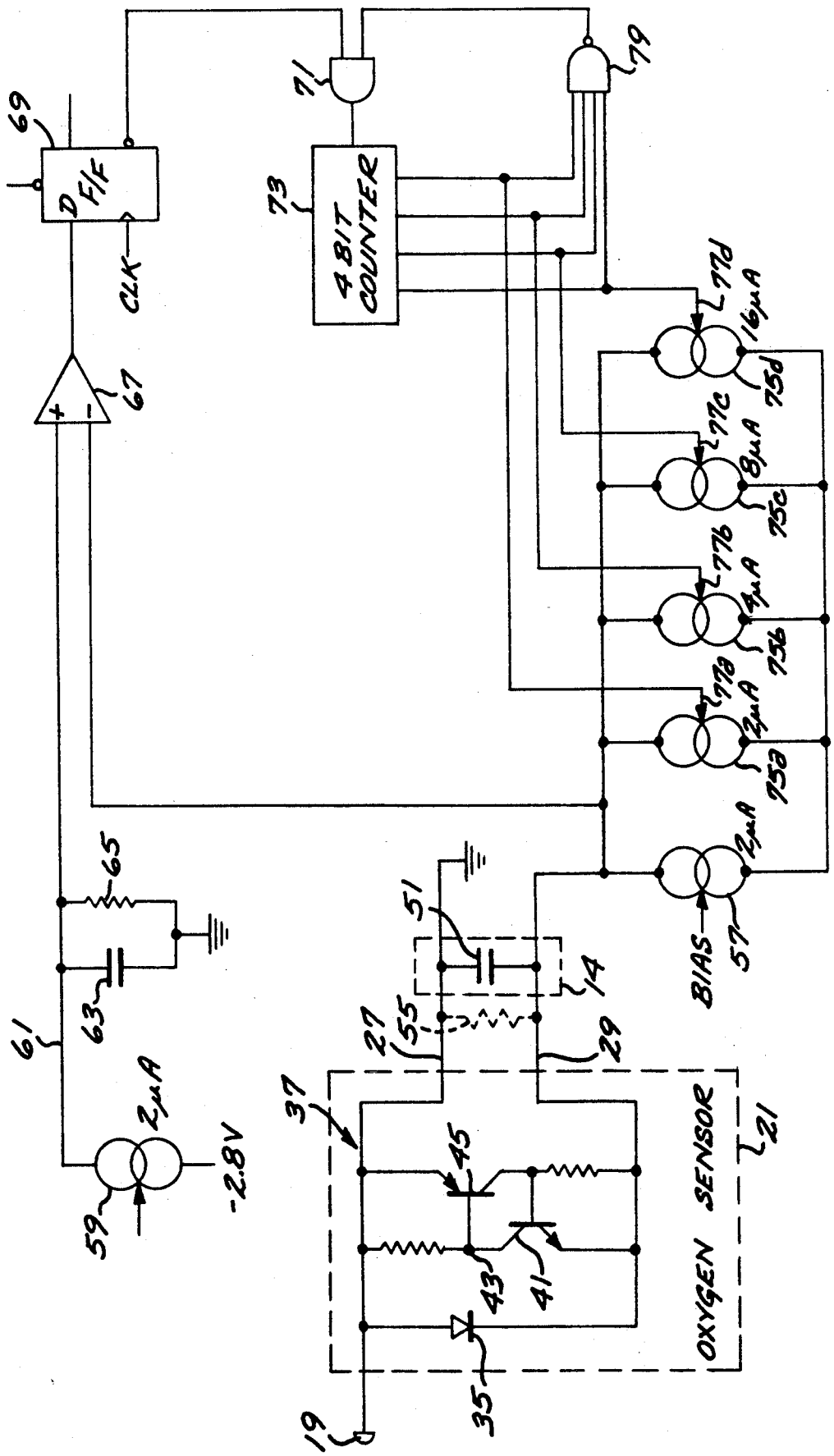
FIG. 4 is a schematic diagram of a first embodiment of the sensor drive and sensor process circuits of FIG. 2, shown in combination with the oxygen sensor.

FIG. 4 depicts the relevant portions of a first embodiment of the sensor drive circuit 25 and sensor process circuit 31, for compensating for an unspecified leakage resistance 55 arranged in parallel with the feedthrough capacitor 51 and oxygen sensor 21. The depicted circuit includes two identical current sources 57 and 59 for supplying identical currents (e.g., 2 microamps), one being coupled over the conductor 29 to the feedthrough capacitor and the oxygen sensor, and the other being coupled over line 61 to a parallel-connected capacitor 63 and resistor 65. The capacitor 63 is selected to have the same capacitance as the feedthrough capacitor 51 (e.g., 4.7 nanofarads). The resistor 65 is utilized to discharge the capacitor 51 after each measurement cycle.

Figure 5A:
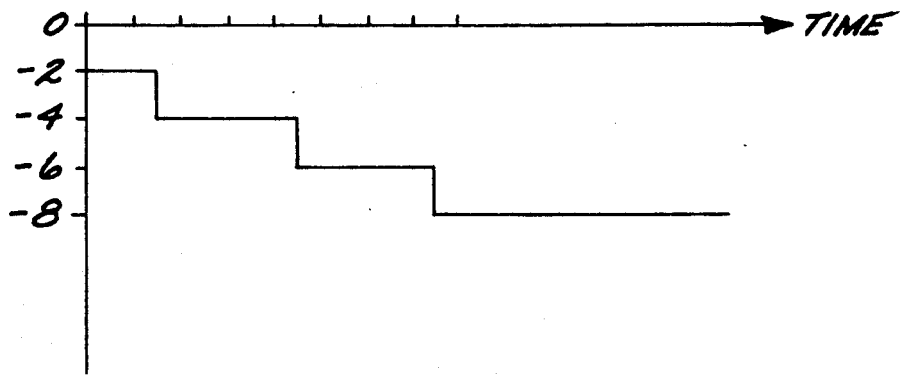
FIGS. 5(a) and (b) are timing diagrams of the electrical current, and resulting voltage, respectively, supplied to the oxygen sensor by the sensor drive circuit of FIG. 4.
Figure 5B:
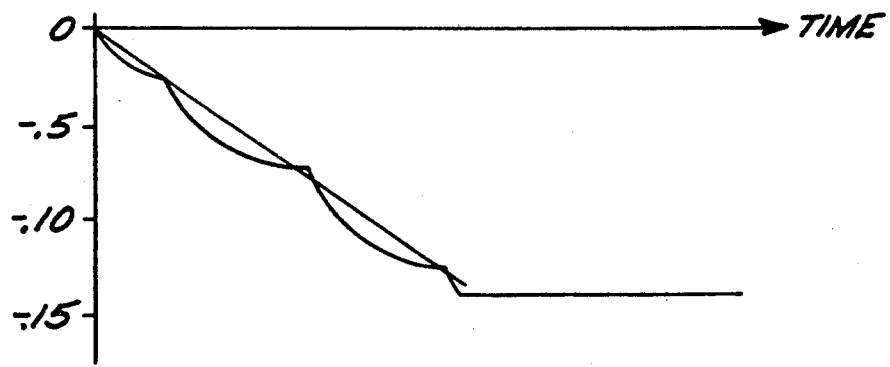

The voltage on the capacitor 63 will increase according to an inverse exponential function determined by the resistance and capacitance value. For the short time duration involved, this charging is substantially linear, as shown in FIG. 5(b). Similarly, the voltage across the feedthrough capacitor 51 will increase according to an inverse exponential function determined by the feedthrough capacitor's capacitance and the leakage resistance 55.

A comparator 67 compares the voltages present on the capacitor 63 and the feedthrough capacitor 51. If the leakage resistance 55 is less than the resistance of the resistor 65, the voltage on the feedthrough capacitor 51 will shortly become less than the voltage on the capacitor 63. The comparator senses this difference and outputs an appropriate level that is clocked into a flip-flop 69. The flip-flop, in turn, outputs a signal that is coupled through a gate 71 to increment a 4-bit counter 73. Four separate current sources 75a, 75b, 75c and 75d are separately controlled by the counter's four digital outputs, via control lines 77a, 77b, 77c and 77d, respectively. These current sources, which provide currents in a binary progression, are connected to the conductor 29 in such a way that they supplement the initial current source 57. Each successive step of the binary progression adds about 2 microamps of current.

When the 4-bit counter 73 is initially incremented, it switches on the first current source 75a, which effectively doubles the current supplied to the feedthrough capacitor 51 and oxygen sensor 21. This increases the rate at which the feedthrough capacitor charges, driving it closer to the continuously-increasing voltage of the capacitor 63. This is depicted in FIG. 5(b).

So long as the voltage on the feedthrough capacitor 51 remains less than the voltage on the capacitor 65, the comparator 67 will continue to increment the counter 73 each time the flip-flop 69 is clocked. With each such incrementing, an additional amount of current will be supplied over the conductor 29 to the feedthrough capacitor and oxygen sensor 21. On the other hand, if the voltage on the feedthrough capacitor 51 exceeds the voltage on the capacitor 65, the counter will not be incremented and the current being supplied to the feedthrough capacitor will remain the same. FIG. 5(a) depicts the current supplied to the feedthrough capacitor for one exemplary intermediate value for the leakage resistance 55. A gate 79 inhibits further incrementing of the counter if it ever reaches its maximum count.

After a time period corresponding to 16 clock pulses has elapsed, it is known that the voltage on the capacitor 65, and thus the voltage on the feedthrough capacitor 51, should have reached the prescribed voltage slightly less than the onset voltage of the LED 35. This voltage is preferably about 1.35 volts. At this time, the coupling of further clock pulses to the flip-flop 69 is terminated, while the current source 57 and as many as all of the current sources 75a, 75b, 75c and 75d continue to supply current to the feedthrough capacitor and oxygen sensor 21. The current, which is all conducted through the LED, is insufficient to cause the LED to emit light.

During this time, the voltage at the integrating node 43 of the oxygen sensor 21 is allowed to decay to near zero, by discharging through the resistor $R_1$ 47. After a predetermined time interval, the node voltage will be fully discharged and the oxygen sensor will be properly initialized and in condition to receive the current pulse 39, described above.

Because of the controllably increased current supplied to the feedthrough capacitor 51 and oxygen sensor 21, this proper initialization is reached despite the presence of a leakage resistance 55 that can vary over a wide range. The added current provided by the current sources 75a, 75b, 75c and 75d substantially compensates for this leakage resistance by supplying whatever current is required to prevent the resistance from robbing from the feedthrough capacitor the current supplied to it by the current source 57.

Figure 6:
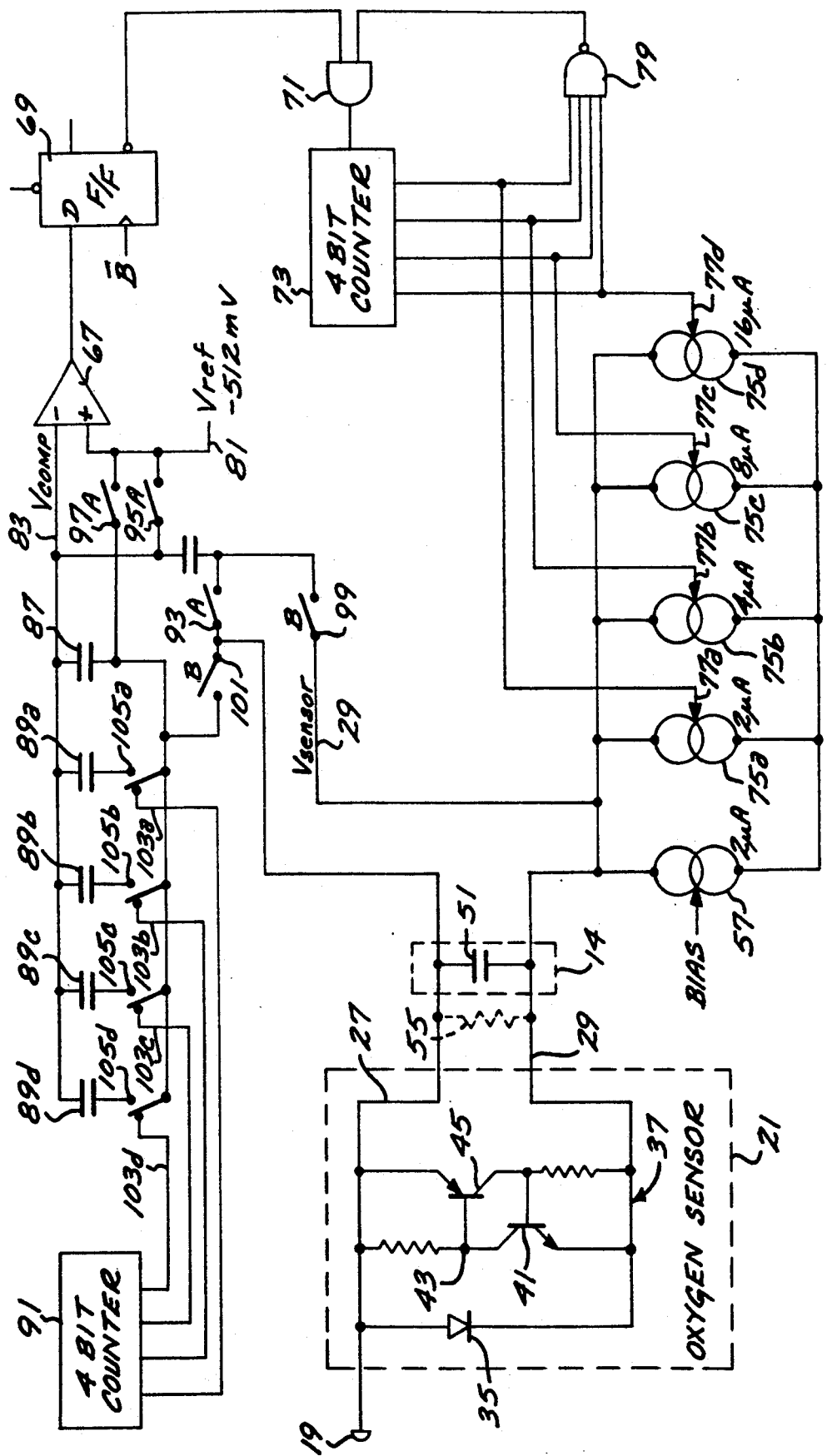
FIG. 6 is a block diagram of an alternative embodiment of the sensor drive and sensor process circuits, shown in combination with the oxygen sensor.
Figure 7A:
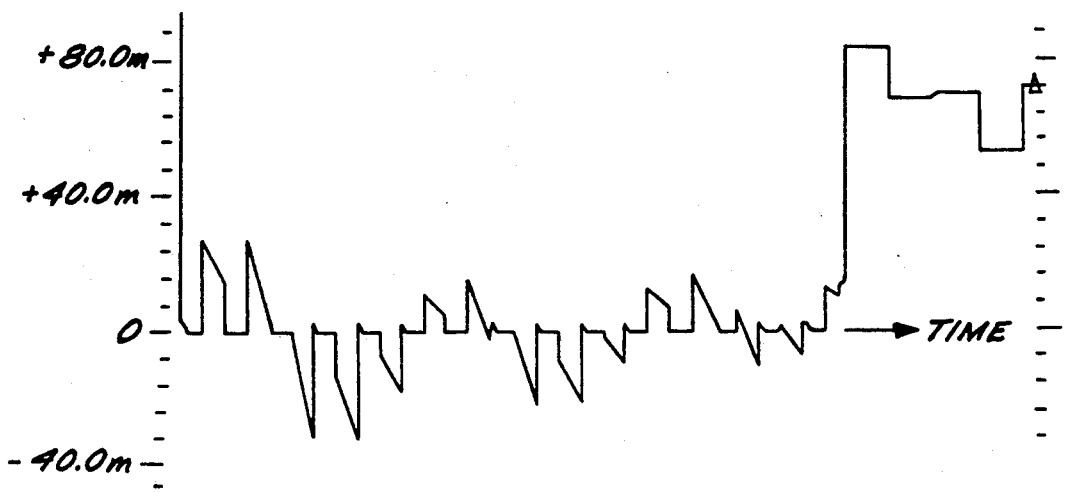
FIG. 7(a) is a timing diagram of the voltage signal supplied to the comparator of FIG. 6, and FIGS. 7(b) and (c) are timing diagrams of the electrical current, and resulting voltage, respectively, applied to the oxygen sensor by the sensor drive circuit of FIG. 6, all for one typical value for the parallel leakage resistance.
Figure 7B:
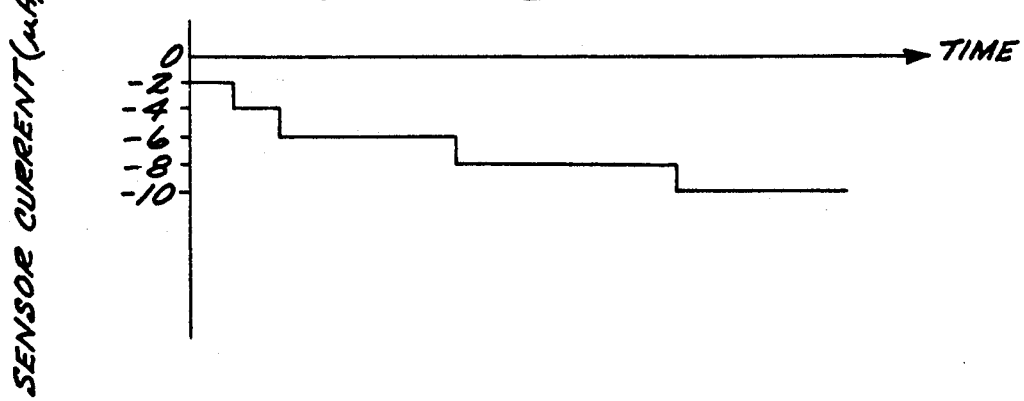
Figure 7C:
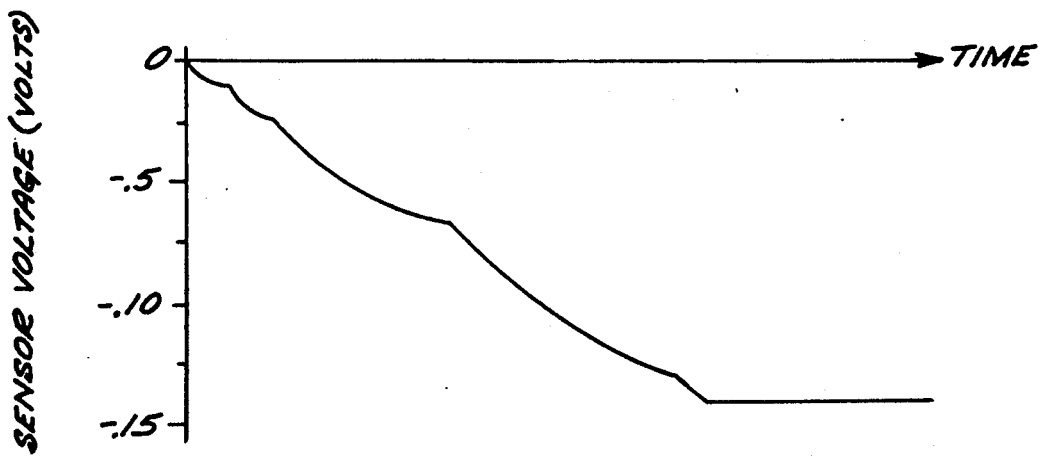

FIG. 6 depicts a portion of the sensor drive circuit 25 and sensor process circuit 31 in accordance with a second embodiment of the invention. This embodiment is similar to the first embodiment of FIG. 4, except that no reference voltage ramp is used. Instead, additional capacitance is switched into the circuit periodically, and a specific voltage, $V_{comp}$, is compared to a reference voltage, $V_{ref}$, periodically. If the magnitude of $V_{comp}$ is at least that of $V_{ref}$, the system is operating well. If not, then additional current is supplied to compensate. In FIG. 6, all of the circuit elements that are the same as those of the FIG. 4 embodiment are identified by the same reference numerals.

In FIG. 6, the comparator 67 receives at its non-inverting input terminal the fixed reference voltage, supplied on line 81, and receives at its inverting input terminal, on line 83, the voltage $V_{comp}$. The capacitively-divided voltage is provided by a series capacitor 85 and parallel-connected capacitors 87 and 89a, 89b, 89c and 89d. The capacitance values of the four capacitors 89a, 89b, 89c and 89d follow a binary sequence, and these capacitors are switched into the circuit under the control of a 4-bit counter 91.

Fifteen clock cycles are required for the circuit to charge the feedthrough capacitor 51 to its predetermined voltage. (The number fifteen is used in the preferred embodiment, and may vary.) Prior to first of such cycles, the capacitors are initialized by closing three A switches 93, 95 and 97 and by opening two B switches 99 and 101. In this condition, the reference voltage supplied on line 81 is applied to both input terminals of the comparator 67, and a zero-volt reference is applied to the input side of the series capacitor 85.

The A and B switches are controlled by complementary A and B clock signals, respectively. (Note that the timing is such that the A switches are never closed at the same time as the B switches.) Thereafter, the A switches 93, 95 and 97 are opened and the B switches 99 and 101 are closed, which results in the reference voltage being applied only to the comparator's non-inverting input terminal and the feedthrough capacitance voltage being applied to the input side of the series capacitor 85, with that voltage then being divided in accordance with the capacitance ratio of the capacitor 85 and the capacitor 87.

During each successive clock cycle, the flip-flop 69 is clocked by the A clock signal and the 4-bit counter 91 is clocked by the B clock signal. In addition, the A switches 93, 95 and 97 and the B switches 99 and 101 are operated, as described above. The four digital output signals of the counter 91 are coupled over lines 103a, 103b, 103c and 103d to switches 105a, 105b, 105c and 105d associated with the respective capacitors 89a, 89b, 89c and 89d. Thus, with each successive cycle, a stepped increase in parallel capacitance is provided. The system can best be analyzed by using a charge conservation equation as follows:

$$V_{comp} = \frac{5.9 \ (V_{ref} + V_{sensor})}{6.6 + n}$$

where n is the number of units of capacitance switched in. If the system is operating properly, $V_{comp}$ should equal or exceed $V_{ref}$ in magnitude. In this situation, no additional current need be supplied by the current source. Note that flip-flop 69 is set at each clock pulse prior to reading the output of the comparator 67.

If the feedthrough capacitor voltage, $V_{comp}$, is ever determined by the comparator 67 to be less in magnitude than the reference voltage, $V_{ref}$, supplied on line 81, this resets the flip-flop 69, which in turn increments the 4-bit counter 73. An incrementally higher current is thereby supplied by the current sources 75a, 75b, 75c and 75d to the feedthrough capacitor 51 and oxygen sensor 21. As with the embodiment of FIG. 4, this embodiment likewise continues to increase the current being supplied each time it is determined that the feedthrough capacitor voltage is insufficiently high. On the other hand, each time it is determined at a clock cycle that the feedthrough capacitor voltage then exceeds its desired voltage, the electrical current previously supplied through the feedthrough capacitor remains unchanged.

After fifteen clock pulses, further incrementing of the electrical current being supplied to the feedthrough capacitor 51 and oxygen sensor 21 is terminated. The circuit then idles for a predetermined time period, allowing the voltage on the integrating node 43 of the phototransistor circuit 37 to decay to zero. Thereafter, a current pulse 39 can be applied to the oxygen sensor, allowing it to properly detect blood oxygen saturation level, as described above.

It should be appreciated from the foregoing description that the present provides an improved blood oxygen sensor apparatus having a special leakage compensation circuit that allows proper initialization of the oxygen sensor regardless of the value of any leakage resistance that might be present in parallel with the oxygen sensor. During an initialization mode, in which a capacitor arranged in parallel with oxygen sensor is charged by a small initialization current, the leakage compensation circuit monitors the capacitor voltage and controllably increases the current if it is determined that the capacitor is charging at an insufficient rate, due to unspecified leakage resistance. This enables the oxygen sensor to be properly initialized such that it can thereafter accurately measure blood oxygen saturation levels.

Although the invention has been described in detail with reference only to the presently-preferred embodiments, those of ordinary skill in the art will appreciate that various modifications can be made without departing from the invention. Accordingly, the invention is defined only by the following claims.

What is claimed is:

1. A leakage compensation circuit for use in a blood oxygen sensor of the kind that includes a light-emitting diode for selectively illuminating the blood and a photosensor for sensing the intensity of light reflected by the blood, wherein the light-emitting diode has a capacitor and leakage resistance arranged in parallel with it, the leakage compensation circuit comprising:

initialization means for supplying an initialization current during an initialization mode to controllably charge the capacitor arranged in parallel with the light-emitting diode to a predetermined voltage that is less than an onset voltage at which the light-emitting diode emits substantial light, wherein the initialization means includes means for controllably increasing the initialization current with time, to compensate for the presence of the leakage resistance in parallel with the capacitor; and pulse means for supplying a light-generating current to the light-emitting diode during a measurement mode, which follows the initialization mode, the light-generating current being substantially greater than the initialization current, such that the light-emitting diode emits substantial light for reflection by the blood and sensing by the photosensor;

wherein the charging of the capacitor to the predetermined voltage during the initialization mode facilitates the emission by the light-emitting diode of a more well-defined amount of light and the generation by the sensor of an accurate measurement of blood oxygen saturation.

2. A leakage compensation circuit as defined in claim 1, wherein the initialization means is operable to charge the capacitor to the predetermined voltage substantially linearly.

3. A leakage compensation circuit as defined in claim 2, wherein the initialization means comprises:
means for generating a voltage ramp reference signal; and
means for comparing the capacitor voltage with the ramp reference signal and for adjusting the initialization current in discrete steps in accordance with the outcome of the comparison.

4. A leakage compensation circuit as defined in claim 2, wherein the initialization means comprises means for comparing the capacitor voltage with a predetermined reference at a series of discrete times and for adjusting the initialization current at those discrete times in accordance with the outcome of the successive comparisons.

5. A leakage compensation circuit as defined in claim 4, wherein the means for comparing and adjusting comprises means for generating a voltage ramp signal that constitutes the predetermined reference.

6. A leakage compensation circuit as defined in claim 1, wherein the initialization means comprises:
means for monitoring the capacitor voltage at a series of discrete times and for producing an adjusted voltage indicative of the state of the capacitor voltage at the series of discrete times; and
means for comparing the adjusted voltage signal with a fixed reference voltage at the series of discrete times and for adjusting the initialization current at those discrete times in accordance with the successive comparisons.

7. A leakage compensation circuit as defined in claim 1, wherein:
the leakage resistance has a non-predetermined value within a predetermined range; and
the initialization means comprises means for controllably increasing the initialization current so as to charge the capacitor to the predetermined voltage regardless of the value of the leakage resistance.

8. A blood oxygen sensor apparatus for use with a pacemaker, comprising:
a light-emitting diode positioned such that its emitted light is directed at blood whose oxygen saturation level is to be measured, wherein a capacitor and leakage resistance are arranged in parallel with the light-emitting diode;
a photodetector positioned to detect light emitted by the light-emitting diode and reflected by the blood and to produce a corresponding intensity signal;
detection means responsive to the intensity signal, for determining the blood's oxygen content; and
initialization means for supplying an initialization current during an initialization mode to charge the capacitor substantially linearly to a predetermined voltage that is less than an onset voltage at which the light-emitting diode emits substantial light, wherein the initialization means includes means for controllably increasing the initialization current with time, to compensate for the presence of the leakage resistance, and wherein the charging of the capacitor to the predetermined voltage during the initialization mode facilitates the emission by the light-emitting diode of a well-defined amount of light and the generation by the apparatus of an accurate measurement of blood oxygen saturation and means for driving said LED.

9. A blood oxygen sensor apparatus as defined in claim 8, wherein the initialization means comprises:
means for generating a voltage ramp reference signal; and
means for comparing the capacitor voltage with the ramp reference signal and for adjusting the initialization current in discrete steps in accordance with the outcome of the comparison.

10. A blood oxygen sensor apparatus as defined in claim 8, wherein the initialization means comprises means for comparing the capacitor voltage with a predetermined reference at a series of discrete times and for adjusting the initialization current at those discrete times in accordance with the outcome of the successive comparisons.

11. A blood oxygen sensor apparatus as defined in claim 10, wherein the means for comparing and adjusting comprises means for generating a voltage ramp signal that constitutes the predetermined reference.

12. A blood oxygen sensor apparatus as defined in claim 8, wherein the initialization means comprises:
means for monitoring the capacitor voltage at a series of discrete times and for producing an adjusted voltage indicative of the state of the capacitor voltage at the series of discrete times; and
means for comparing the series of adjusted voltage signals with a fixed reference voltage at the series of discrete times and for adjusting the initialization current at those discrete times in accordance with the successive comparisons.

13. A blood oxygen sensor apparatus as defined in claim 12, wherein the means for comparing and adjusting comprises:
a comparator having as inputs the adjusted voltage and the fixed reference voltage.

14. A blood oxygen sensor apparatus as defined in claim 13, wherein the means for comparing and adjusting adjusts the initialization current whenever the adjusted voltage is less than the fixed reference voltage.

15. A blood oxygen sensor apparatus as defined in claim 12, wherein the means for monitoring comprises:
a first test capacitor having a fixed value, the first test capacitor having a first terminal and a second terminal, the first terminal of the first test capacitor being connected to the capacitor; and
a second test capacitor having a variable value, the second test capacitor having a first terminal and a second terminal, the second terminal of the first test capacitor being connected to the first terminal of the second test capacitor and serving as the point at which the adjusted voltage is measured, the second terminal of the second test capacitor being connected to the fixed reference voltage.

16. A blood oxygen sensor apparatus as defined in claim 15, additionally comprising:

means for incrementally increasing the value of the second test capacitor between each of the series of discrete times.

17. A blood oxygen sensor apparatus as defined in claim 16, additionally comprising:
   means for precharging the first test capacitor prior to each of the series of discrete times; and
   means for discharging the second test capacitor prior to each of the series of discrete times.

18. A blood oxygen sensor apparatus as defined in claim 8, wherein:
   the leakage resistance has a non-predetermined value within a predetermined range; and
   the initialization means comprises means for controllably increasing the initialization current so as to charge the capacitor to the predetermined voltage regardless of the value of the leakage resistance.

19. A blood oxygen sensor apparatus as defined in claim 8, wherein:
   wherein said means for driving said LED, comprises pulse means for supplying a light-generating current to the light-emitting diode during a measurement mode, which follows the initialization mode, the light-generating current being substantially greater than the initialization current, such that the light-emitting diode emits substantial light for reflection by the blood and sensing by the photodetector;
   the detection means comprises
      integrator means for integrating the intensity signal produced by the photodetector, to produce an integrated intensity signal, and
      comparator means for comparing the integrated voltage signal with a predetermined threshold and for providing an output signal at a detection time when the integrated voltage signal reaches the threshold, the time delay from initiation of the measurement mode until the detection time being inversely related to the blood's oxygen saturation level.

20. A blood oxygen sensor apparatus as defined in claim 19, wherein:
   the comparator means is configured such that, when the integrated voltage signal reaches the predetermined threshold, it accepts a substantial portion of the light-generating current supplied by the pulse means and therefore reduces the voltage applied to the light-emitting diode below the onset voltage; and
   the detection means further comprises means for monitoring the voltage applied to the light-emitting diode and for establishing the detection time when the voltage is reduced below the onset voltage.

21. A blood oxygen sensor apparatus as defined in claim 19, wherein:
   the photodetector comprises a phototransistor; and
   the integrator means and comparator means together comprise:
      a transistor having its collector terminal connected to the base terminal of the phototransistor, its base terminal connected to the collector terminal of the phototransistor, and its emitter terminal connected to a first terminal of the light-emitting diode, the emitter terminal of the phototransistor being connected to a second terminal of the light-emitting diode,
      a first resistor connected between the base and emitter terminals of the transistor, and
      a second resistor connected between the base and emitter terminals of the phototransistor.

22. A blood oxygen sensor apparatus as defined in claim 21, wherein:
   the transistor is a pnp transistor and the phototransistor is an npn transistor;
   the resistance of the first resistor is substantially larger than the resistance of the second resistor; and
   the first terminal of the light-emitting diode is its anode, and the second terminal of the light-emitting diode is its cathode.

23. A blood oxygen sensor apparatus as defined in claim 22, wherein the initialization current supplied to the light-emitting diode by the initialization means is insufficient to develop a voltage drop across the first resistor sufficient to bias on the transistor.

24. A method for use with a heart pacemaker in sensing blood oxygen content, comprising steps of:
   positioning a light-emitting diode such that its emitted light is directed at blood whose oxygen saturation level is to be measured, and a capacitor in parallel with the light-emitting diode, with leakage resistance also being arranged in parallel with the capacitor;
   positioning a photodetector so as to detect light emitted by the light-emitting diode and reflected by the blood, thereby producing a corresponding intensity signal;
   monitoring the intensity signal, to determine the blood's oxygen content; and
   supplying an initialization current during an initialization mode to charge the capacitor to a predetermined voltage that is less than an onset voltage at which the light-emitting diode emits substantial light, wherein the step of supplying includes a step of controllably increasing the initialization current with time, to compensate for the presence of leakage resistance;
   wherein the charging of the capacitor to the predetermined voltage in the step of supplying facilitates the emission by the light-emitting diode of a well-defined amount of light and the generation in the step of monitoring of an accurate measurement of blood oxygen saturation.

25. A method as defined in claim 24, wherein the step of supplying charges the capacitor to the predetermined voltage substantially linearly.

26. A method as defined in claim 24, wherein the step of supplying comprises the steps of:
   generating a voltage ramp reference signal; and
   comparing the capacitor voltage with the ramp reference signal and adjusting the initialization current in discrete steps in accordance with the outcome of the comparison.

27. A method as defined in claim 24, wherein the step of supplying comprises the steps of comparing the capacitor voltage with a predetermined reference at a series of discrete times and adjusting the initialization current at those discrete times in accordance with the outcome of the successive comparisons.

28. A method as defined in claim 27, wherein the steps of comparing and adjusting comprise a step of generating a voltage ramp signal that constitutes the predetermined reference.

29. A method as defined in claim 27, wherein the step of supplying comprises the steps of:

monitoring the capacitor voltage at a series of discrete times and producing an adjusted voltage indicative of the state of the capacitor voltage at the series of discrete times; and comparing the series of adjusted voltage signals with a fixed reference voltage at the series of discrete times and adjusting the initialization current at those discrete times in accordance with the successive comparisons.

30. A method as defined in claim 24, wherein:

the leakage resistance has a non-predetermined value within a predetermined range; and the step of supplying comprises a step of controllably increasing the initialization current so as to charge the capacitor to the predetermined voltage, thereby compensating for the value of the leakage resistance.

31. A method as defined in claim 24, wherein:

the method further comprises a step of supplying a light-generating current to the light-emitting diode during a measurement, which follows the initialization mode, the light-generating current being substantially greater than the initialization current, such that the light-emitting diode emits substantial light for reflection by the blood and sensing by the photodetector; and the step of monitoring comprises the steps of:

integrating the intensity signal produced by the photodetector, to produce an integrated intensity signal, and comparing the integrated voltage signal with a predetermined threshold and providing an output signal at a detection time when the integrated voltage signal reaches the threshold, the time delay from initiation of the measurement mode until the detection time being inversely related to the blood's oxygen saturation level.

32. A blood oxygen content sensor apparatus for use with a pacemaker, comprising:

a light-emitting diode positioned such that its emitted light is directed at blood whose oxygen saturation level is to be measured, wherein a capacitor and leakage resistance are arranged in parallel with the light-emitting diode, the leakage resistance having a non-predetermined value within a predetermined range;

a phototransistor positioned to detect light emitted by the light-emitting diode and reflected by the blood and to produce a corresponding intensity signal;

detection means responsive to the intensity signal, for determining the blood's oxygen content;

initialization means for supplying an initialization current to the light-emitting diode during an initialization mode, to charge the capacitor substantially linearly to a predetermined voltage substantially the same as, but slightly less than, an onset voltage at which the light-emitting diode emits substantial light; and pulse means for supplying a light-generating current to the light-emitting diode during a measurement mode, following the initialization mode, the light-generating current being substantially greater than the initialization current, such that the light-emitting diode emits substantial light for reflection by the blood and sensing by the phototransistor;

wherein the detection means includes:

integrator means for integrating the intensity signal produced by the photodetector during the measurement mode, to produce an integrated intensity signal, comparator means for comparing the integrated voltage signal with a predetermined threshold and, when the integrated voltage signal reaches the predetermined threshold, for accepting a substantial portion of the light-generating current supplied by the pulse means, thereby reducing the voltage applied to the light-emitting diode below the onset voltage, and means for monitoring the voltage applied to the light-emitting diode and for establishing a detection time when the voltage is reduced below the onset voltage, the time delay from initiation of the measurement mode until the detection time being inversely related to the blood's oxygen saturation level;

wherein the charging of the capacitor to the predetermined voltage during the initialization mode facilitates the emission by the light-emitting diode of a well-defined amount of light and the generation by the apparatus of an accurate measurement of blood oxygen content.

33. A blood oxygen content sensor apparatus as defined in claim 32, wherein the initialization means comprises means for comparing the capacitor voltage with a predetermined reference at a series of discrete times and for adjusting the initialization current at those discrete times in accordance with the outcome of the successive comparisons.

34. A blood oxygen content sensor apparatus as defined in claim 33, wherein the means for comparing and adjusting comprises means for generating a voltage ramp signal that constitutes the predetermined reference.

35. A blood oxygen content sensor apparatus as defined in claim 33, wherein the means for comparing and adjusting comprises:

means for monitoring the capacitor at the series of discrete times and for producing an adjusted voltage indicative of the state of the capacitor voltage at the series of discrete times; and means for comparing the series of adjusted voltage signals with a fixed reference voltage at the series of discrete times and for adjusting the initialization current at those discrete times in accordance with the successive comparisons.

* * * * *